(12) United States Patent
Steen et al.

(10) Patent No.: US 10,357,029 B2
(45) Date of Patent: Jul. 23, 2019

(54) INSERT FOR AN ORGAN TRANSPORT DEVICE

(71) Applicant: VIVOLINE MEDICAL AB, Lund (SE)

(72) Inventors: Stig Steen, Lund (SE); Audrius Paskevicius, Lund (SE); Anna Beyer, Lund (SE); Benjamin King, Takaka (NZ)

(73) Assignee: VIVOLINE MEDICAL AB, Lund (SE)

( * ) Notice: Subject to any disclaimer, the term of this patent is extended or adjusted under 35 U.S.C. 154(b) by 2 days.

(21) Appl. No.: 15/108,942

(22) PCT Filed: Dec. 29, 2014

(86) PCT No.: PCT/SE2014/000160
§ 371 (c)(1),
(2) Date: Jun. 29, 2016

(87) PCT Pub. No.: WO2015/102524
PCT Pub. Date: Jul. 9, 2015

(65) Prior Publication Data
US 2016/0324145 A1 Nov. 10, 2016

(30) Foreign Application Priority Data
Dec. 30, 2013 (SE) ........................................ 1330158

(51) Int. Cl.
*A01N 1/02* (2006.01)

(52) U.S. Cl.
CPC .................................. *A01N 1/0247* (2013.01)

(58) Field of Classification Search
CPC ..................................................... A01N 1/0247
USPC ........................................................ 435/284.1
See application file for complete search history.

(56) References Cited

U.S. PATENT DOCUMENTS

| 5,356,771 | A | 10/1994 | O'Dell |
| 5,362,622 | A | 11/1994 | O'Dell et al. |
| 5,716,378 | A | 2/1998 | Minten |
| 6,527,957 | B1 * | 3/2003 | Deniega ................... A01N 1/02 210/651 |
| 2005/0147958 | A1 * | 7/2005 | Hassanein ................ A01N 1/02 435/1.1 |

(Continued)

FOREIGN PATENT DOCUMENTS

| EP | 0 376 763 A2 | 7/1990 |
| WO | WO 91/14364 A1 | 10/1991 |

(Continued)

*Primary Examiner* — Kevin Joyner
*Assistant Examiner* — Holly M Mull
(74) *Attorney, Agent, or Firm* — Birch, Stewart, Kolasch & Birch, LLP

(57) ABSTRACT

A device for arranging a harvested heart to be stored in an enclosure before transplantation, whereby the heart is connected to a tube for supply of a medical fluid to the heart. A cylindrical insert intended to be arranged in a enclosure for the heart, comprises a fixture for immobilizing the tube in a central position of the insert. The fixture comprises an arm extending from the periphery of the fixture to the center of the fixture; and a jaw device for gripping the tube and maintaining the tube and the organ hanging in the tube in a predetermined height position.

7 Claims, 22 Drawing Sheets

(56) References Cited

U.S. PATENT DOCUMENTS

2011/0212431 A1* 9/2011 Bunegin .............. A01N 1/0247
                                                       435/1.2

FOREIGN PATENT DOCUMENTS

WO    WO-2006118990 A2 * 11/2006 ............... A01N 1/02
WO    WO 2012/128696 A1    9/2012

* cited by examiner

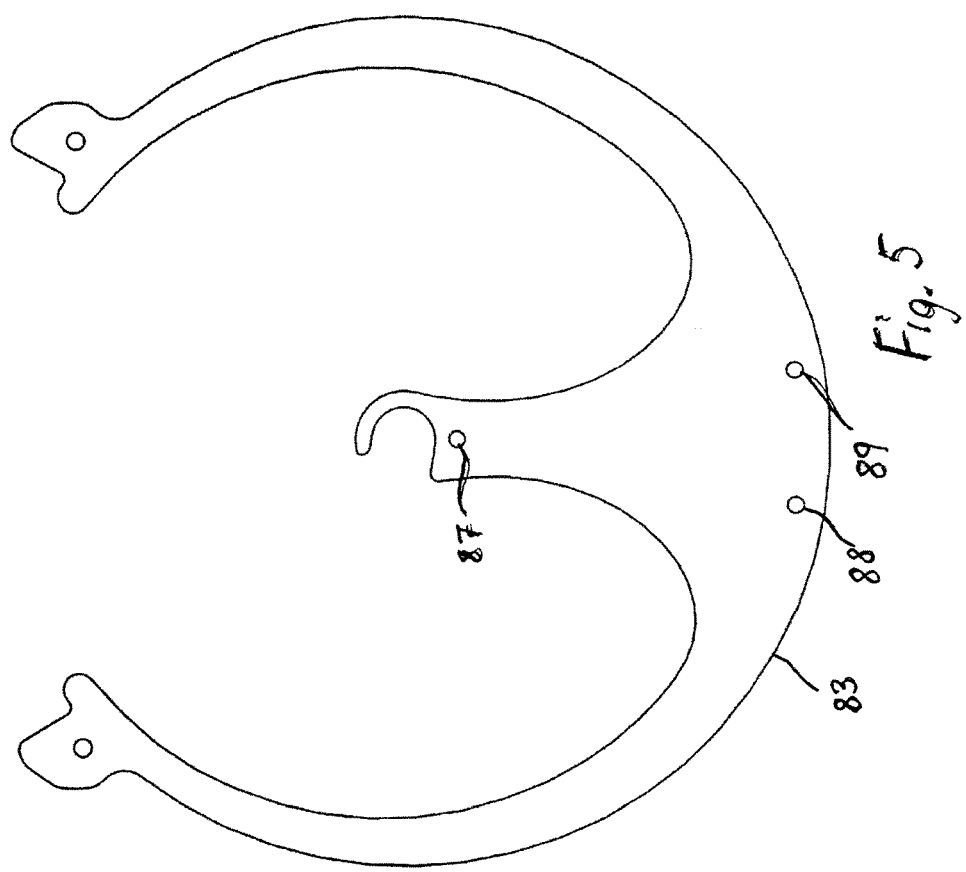
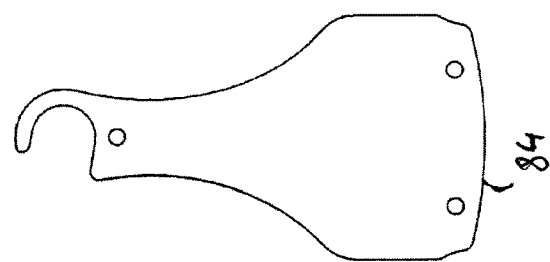
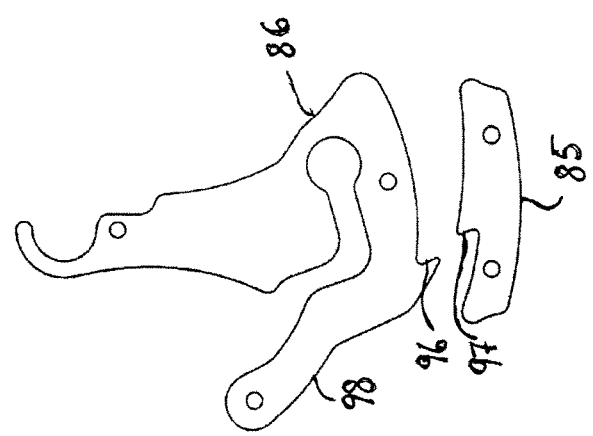
Fig. 5

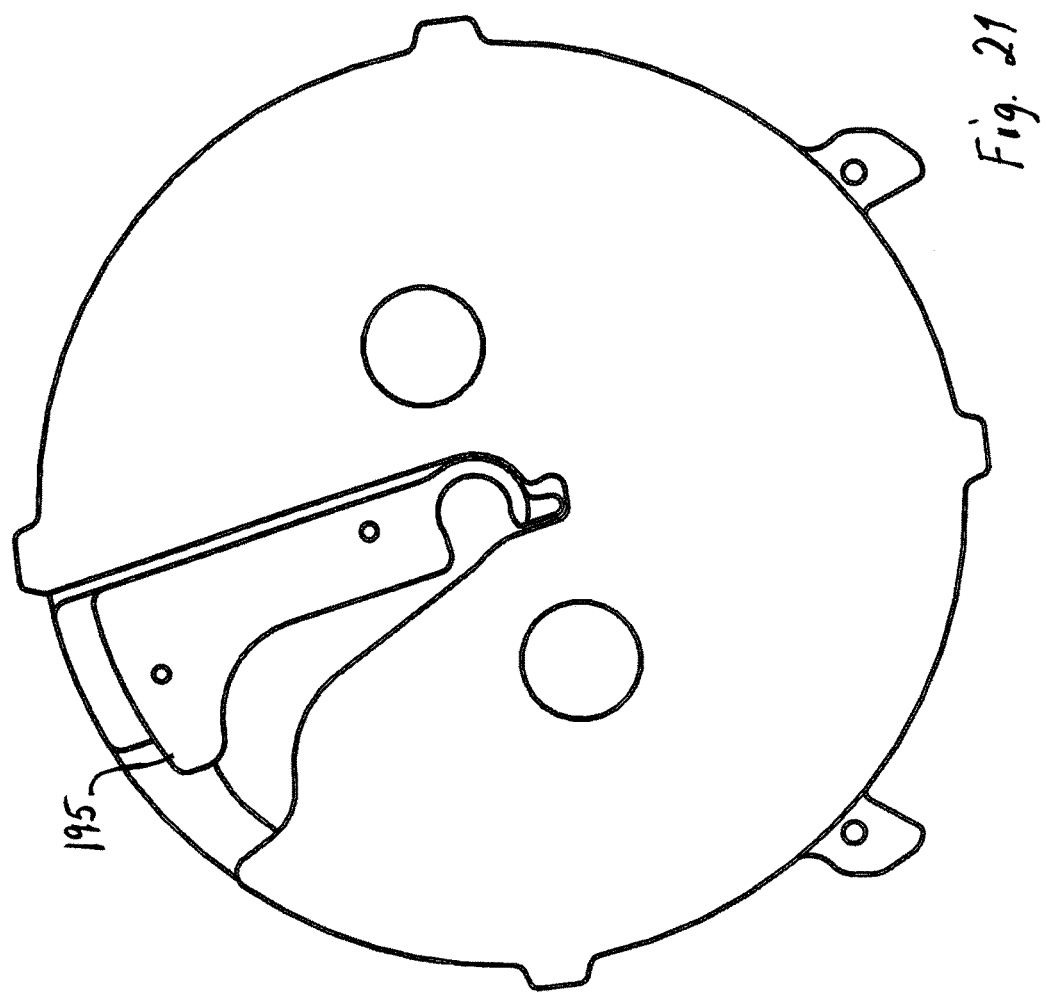

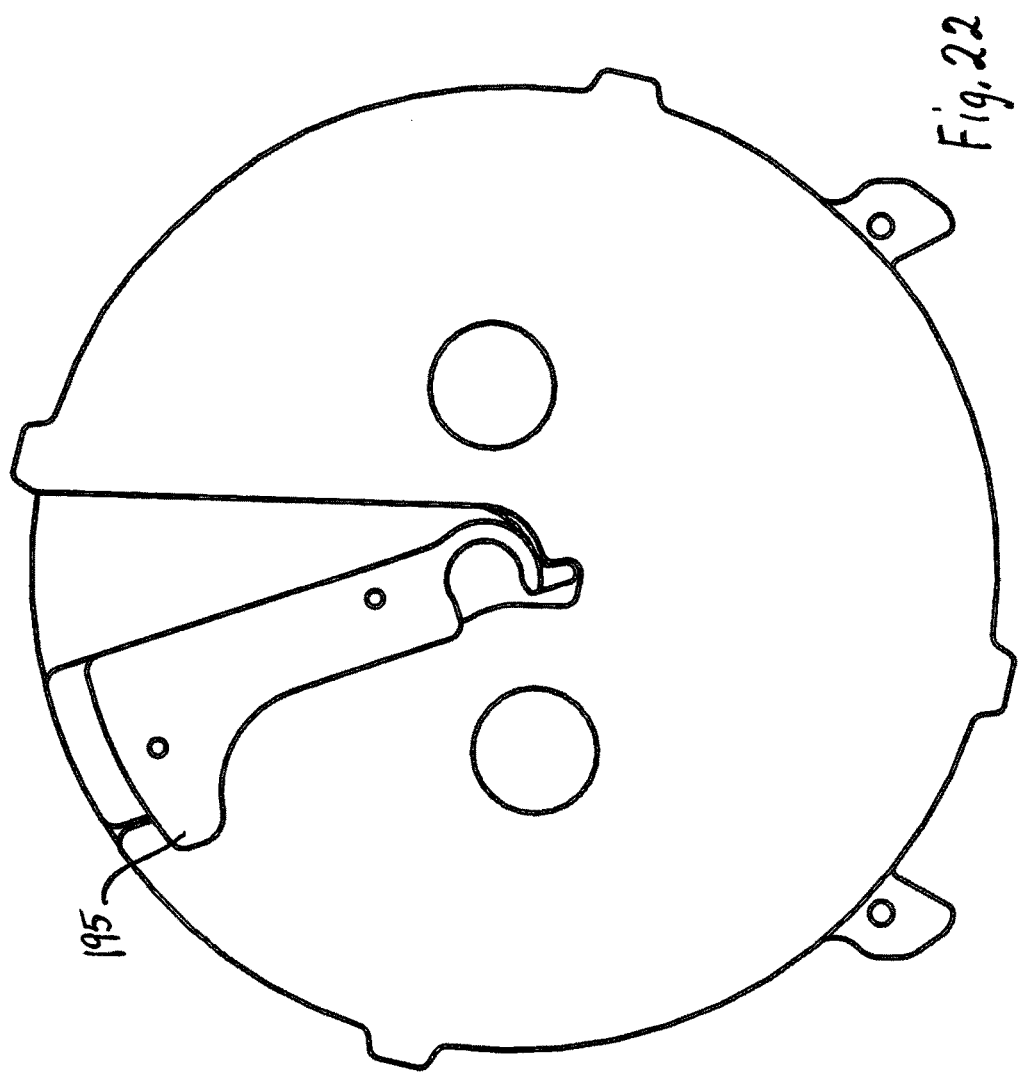

INSERT FOR AN ORGAN TRANSPORT DEVICE

FIELD OF INVENTION

The present invention relates to an device for maintaining an organ, such as a heart, viable and transportable for a long time, such as up to and exceeding 24 hours. In more detail, the invention relates to an insert for use in an organ transport device for transporting and storing of the organ before a transplant thereof.

BACKGROUND OF THE INVENTION

U.S. Pat. No. 7,176,015 discloses a transportable organ preservation system for maintaining an organ viable for successful implantation into a human recipient. The system comprises a cylinder that contains 255 liter of oxygen sufficient for up to 34 hours of perfusion time. The organ is immersed in a perfusion fluid, which is oxygenated and pumped through the coronary vessels of the heart via the aorta of the heart in a retrograde flow. The system containing the heart, the oxygen cylinder, the pump assembly and hoses are all arranged in a tray, which is inserted in a commercial cooler device having cooling blocks and an insulation for maintaining the cylinder and the heart at a temperature of about 4° C. The sterility is maintained by a lid, which closes the cylinder.

The patent publication WO 2011/037511 A1 discloses a method and a device for treatment of a heart after harvesting and before transplantation, in which a perfusion fluid is circulated through the coronary blood vessels of the heart. The perfusion fluid is cardioplegic and comprises an oncotic agent exerting an oncotic pressure larger than about 30 mmHg and the perfusion is performed at a pressure which is at least 15 mmHg and at least 15 mmHg lower than said oncotic pressure. The perfusion may be intermittent. WO 2011/037511 A1 is assigned to the assignee of the present application and its technical contents are included in the present application by reference.

The patent publication WO 2012/128696 A1 discloses an apparatus for enclosing an organ after harvesting and before implantation, comprising: a vessel enclosing a fluid; a connection tube for connecting a fluid flow hose to the organ for passing a fluid to the organ by means of a pump. A degassing hose extending from the connection tube from a position adjacent the connection of the tube with an inlet part of the organ and to said vessel. A pinch valve is arranged in the degassing hose. During a degassing phase, the pinch valve is opened to allow fluid flow from the pump, via the fluid flow hose to the connection tube and via the degassing hose to the vessel for expelling air entrapped in the fluid flow system. A balloon is arranged to prevent fluid flow via the connection tube to the organ during the degassing phase. A sterility arrangement closes the vessel at the top thereof and may be replaced by a second, third etc. sterility arrangement without compromising the sterility. WO 2012/128696 A1 is assigned to the assignee of the present application and its technical contents are included in the present application by reference.

There is a need in the art for an insert, which may facilitate the arrangement of the organ in a correct position in the organ transport system, which insert may be sterilized and be disposable.

SUMMARY OF THE INVENTION

Accordingly, an object of the present invention is to mitigate, alleviate or eliminate one or more of the above-identified deficiencies and disadvantages singly or in any combination.

According to a first aspect, there is provided a device for arranging a harvested organ to be stored in an enclosure before transplantation, whereby the organ is connected to a tube for supply of a medical fluid to the organ, comprising: a substantially cylindrical insert intended to be arranged in the enclosure for the organ; and a fixture for immobilizing the tube in a central position of the insert.

According to an embodiment, the fixture may comprise an arm extending from the periphery of the fixture to the center of the fixture; and a jaw device at the arm for gripping the tube and maintaining the tube in a predetermined height position. In addition, there may be arranged a locking jaw for co-operation with the jaw device for locking the tube against unintentional withdrawal from the jaw device.

According to another embodiment, the device may further comprise two ears arranged at the fixture for co-operation with openings arranged in the insert for maintaining the fixture in a predetermined position in relation to the insert.

According to a further embodiment, the device may further comprise a lid arranged above the fixture for locking the fixture in position and for closing the space below the fixture.

The organ may be a heart and the tube may be attached to an aorta residue of the heart.

BRIEF DESCRIPTION OF THE DRAWINGS

Further objects, features and advantages of the invention will become apparent from the following detailed description of embodiments of the invention with reference to the drawings, in which:

FIG. 5 is an exploded plan view of the fixture of FIG. 4.

FIGS. 20, 21 and 22 are plan views showing a lid to the fixture of the embodiment according to FIGS. 14 and 17.

DETAILED DESCRIPTION OF EMBODIMENTS

Figure 1:
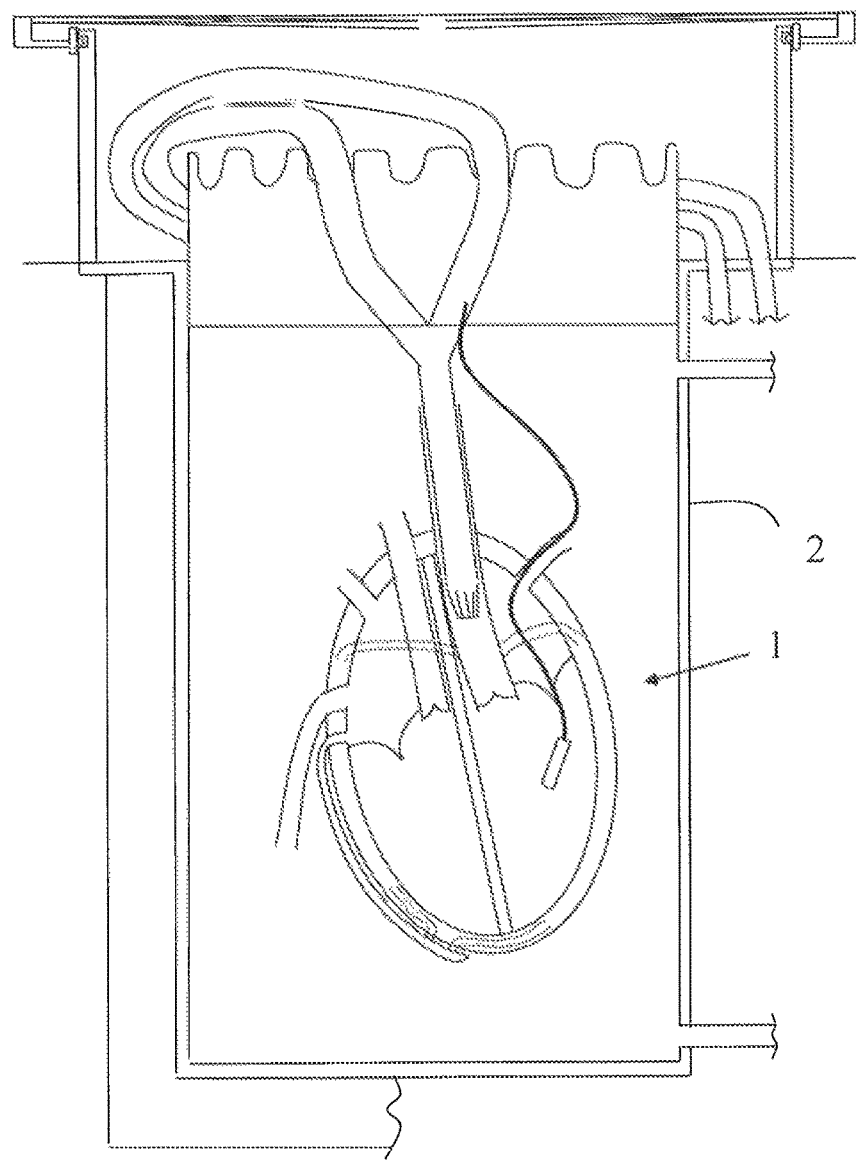
FIG. 1 is a schematic cross-sectional view of a prior art device for storage and transportation of an organ.

Below, several embodiments of the invention will be described. These embodiments are described in illustrating purpose in order to enable a skilled person to carry out the invention and to disclose the best mode. However, such embodiments do not limit the scope of the invention. Moreover, other combinations of the different features are possible within the scope of the invention.

The below embodiments disclose apparatuses and methods for handling an organ between (and including) harvesting the organ in a donor and up to and including implant of the organ in a recipient. While the embodiments are described in connection with a heart to be transplanted, the same device may be used for other organs, such as lungs, liver and kidney.

Most organs cannot withstand a long ischemic time, i.e. a condition without supply of nutrients and oxygen, which are normally supplied via the blood. For example, at normal temperature of 37° C., a heart cannot withstand more than about 20 minutes, while other organs, such as the lungs can withstand up to 40 minutes or more.

The outcome of an organ transplantation is among others dependent on the condition of the organ before harvesting. All efforts should be undertaken to maintain the donor and its organs in as good a condition as possible before harvesting. Such efforts may for example include the method steps and processes disclosed in the patent publication WO 2010/077200 A1, the contents of which are included in its entirety in the present specification by reference. Generally, the methods of this publication involves that the potential donor is treated as vigorously as possible before death, and that circulation and ventilation are maintained after the time the potential donor is declared brain dead, in order to avoid ischemic conditions. After obtaining consent from the potential donor in advance and/or his/her next of kin, the potential donor is treated according to a strategy that maintains the organs in a viable condition, after brain death is declared.

Next, the organs are harvested, most often within 24 hours after declaration of brain death. In some countries, brain death is not defined or authorized as indication of actual death. In such countries, the above-mentioned expression "declaration of brain-death" is intended to encompass any other definition of death or actual death, used in such country. For the purpose of the embodiments, brain death involves that the brain and the brain stem do no longer send any electric stimulation signals to the nerve terminals.

The organs are examined for viability and stored, normally under hypothermic conditions until transplantation.

Finally, the organs are implanted in the recipient.

All steps are important for the final result of the organ transplantation.

The present embodiments generally deal with the procedure between harvesting and implantation of an organ, especially of a heart.

In a presently used procedure, the harvesting of a heart may start with exposing the heart to a cardioplegic and cold saline fluid, which is infused in the heart. The heart stops beating and the circulation stops. The heart may now be in the risk for an ischemic condition, since there is no blood flow. However, the infused fluid may provide sufficient oxygen and nutrients for avoiding ischemic conditions. The heart is made free from the donor and the aorta is cut and maintained with a sufficient length, called the aorta residue.

The heart may be examined for viability, involving, for example, checking for aortic valve insufficiency and other examinations. Aortic valve insufficiency may be examined by adding a fluid to the aorta and examine whether the fluid level decreases. Since the fluid has no other escape way except via the aortic valve, this is a good test of the patency of the aortic valves. It is mentioned that the fluid may escape via the coronary vessels. However, the pressure for passing fluid through the coronary vessels is normally higher than a few centimeter of water pillar, which means that substantially no flow will pass through the coronary vessels during such an aorta valve test. The heart may also be examined by angiographic methods in order to detect defects in the coronary vessels and other problems.

A connector tube is attached to the aorta and the heart is moved to a preservation apparatus and connected in a preservation circuit, for example as described in the above-mentioned U.S. Pat. No. 7,176,015 or the patent publication WO 2010/077200 A1. A preservation solution may be circulated through the coronary vessels via the aorta. The preservation is normally cold in order to cool the heart and maintain the heart in a hypothermic condition. Other strategies may as well be used.

FIG. 1 discloses a device as shown in the prior art patent publication WO 2012/128696 A1 comprising a vessel enclosing a heart to be transplanted. The heart is immersed in a preservation solution. The heart is shown schematically with the a ventricle to the right in the figure and includes an aorta, ending in an aortic valve, which opens into a left ventricle of the heart. A mitral valve connects the ventricle with a left atrium.

During normal operation in the living human body, blood enters the left portion of the heart via four pulmonary veins, one of which is shown in FIG. 1. The blood fills the left atrium and the left ventricle during diastole, while the mitral valve is open and the aortic valve is closed. During contraction, the left atrium is first contracted forcing further blood into the left ventricle. Then, the left ventricle is contracted, whereupon the mitral valve is closed and the aortic valve is opened and the blood is forced out into the body via the aorta.

The right portion of the heart operates in a similar way, while blood enters the right atrium via two veins, superior vena cava and inferior vena cava. During diastole, blood fills the right atrium and right ventricle via tricuspid valve. During contraction of the heart, the blood in the right ventricle is forced to the lungs via pulmonary valve and pulmonary artery.

The heart muscle is provided with blood supply via a left coronary artery and a right coronary artery, each dividing into capillaries. The coronary blood is returned to the right atrium via coronary sinus, which collects blood from several coronary veins, such as middle cardiac vein and great cardiac vein. The coronary sinus opens into the right atrium via Thebesian valve (not shown), which prevents backflow into the coronary sinus.

During harvesting of the heart, the heart may be paralyzed via infusion of a cardioplegic fluid into the coronary circulation of the heart. The cardioplegic fluid is normally cold to induce a hypothermic condition in the heart. The aorta is cut in a position to keep it with a sufficient length so that a tube may be attached to the aorta for antegrade supply of coronary fluid flow.

In FIG. 1, the heart 1 is shown removed from the donor and with a connection member such as a connection tube arranged in the aorta. The heart 1 is immersed in the vessel 2 so that the entire aorta is immersed below a fluid surface, in order to keep the aorta moist. There is only one connection required during the harvesting of the organ, namely between the connection tube and the aorta, which connection can be made relatively quickly.

The connection tube is inserted in the aorta so that the end of the connection tube is above the aortic valve and the openings of the coronary arteries. The coronary arteries open normally between 5 and 10 mm above the aortic valve. Since the aortic valve is closed, all fluid passing through the connection tube flows through the coronary arteries.

Figure 2:
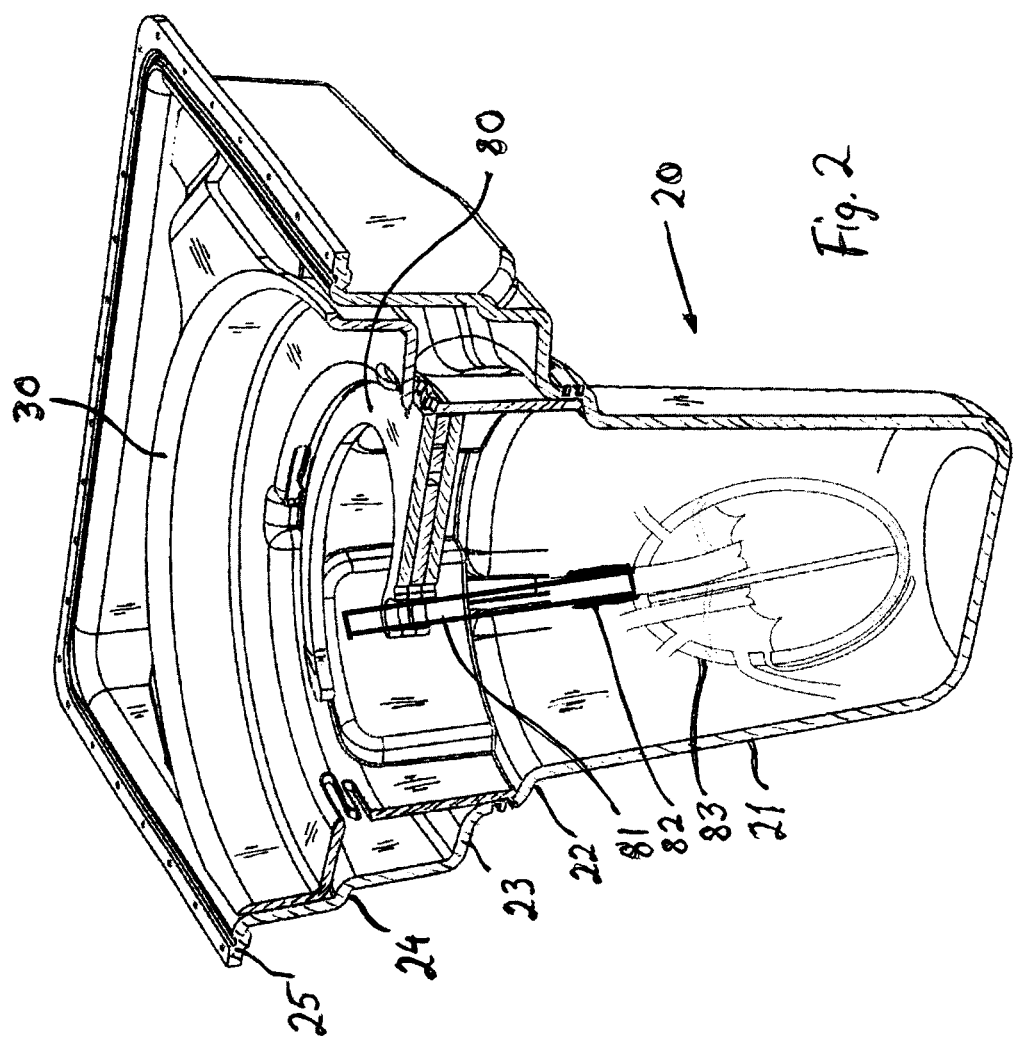
FIG. 2 is a schematic perspective view partially in cross-section of an embodiment of the device according to the invention.

FIG. 2 discloses a modified enclosure for the organ according to an embodiment of the present invention.

The enclosure 20 comprises a lower portion 21, a first shoulder 22, a second shoulder 23 and a third shoulder 24. The third shoulder 24 is connected to a substantially rectangular rim 25. The enclosure 20 fits in a box of the type disclosed in WO 2012/128696 A1. The box comprises pumps, cooling devices, oxygenator, tubes, valves etc for circulating a fluid.

Inside said enclosure 20, there is arranged an insert 30 according to an embodiment of the invention. The insert 30 rests on said first shoulder 22. The insert 30 is provided with legs, one of which is visible in FIG. 2. There are four legs each arranged in a corner inside said rectangular rim 25 and along the side in order to immobilize said insert 30. Thus, the insert is easily inserted into the enclosure 20 from above.

The insert 30 accommodates a fixture 80 for a connection tube 81, which is connected to the residue of the aorta 82 of the heart 83.

Figure 3:
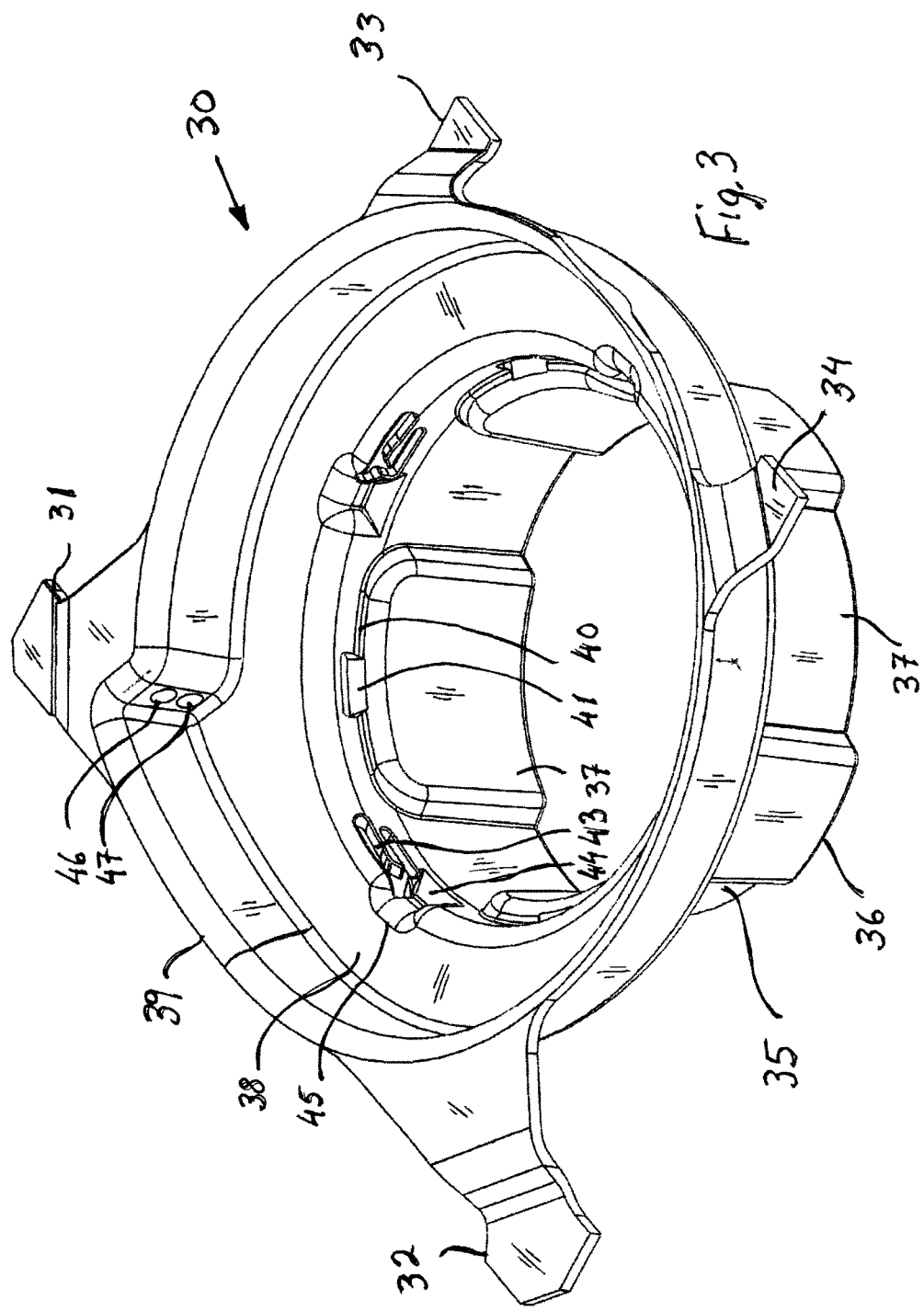
FIG. 3 is a perspective view of an insert in the embodiment shown in FIG. 2.

The insert 30 is shown separately in perspective in FIG. 3.

The bottom portion of the insert 30 is formed of a lower cylindrical portion 35, having a bottom rim 36, which is arranged to rest on shoulder 22 or being arranged just above shoulder 22. The lower cylindrical portion 35 is provided with four recesses 37 leaving an area for any fluid to pass from the space outside the insert 30 to the space below the insert 30.

An annular portion 38 is at its inner side connected to the lower cylindrical portion 35 and an upper cylindrical portion 39 is connected to the outside of the annular portion 38. The upper cylindrical portion 39 is supported by said four legs 31, 32, 33, 34.

The upper portion of each recess 37 forms a shoulder 40. Directly above each recess 37, there is arranged an opening 41 having a substantially rectangular shape. Offset about 45° in relation to said openings 41, there is a set of four slits 43, each having a side entrance 44 via a recess 45.

Figure 4:
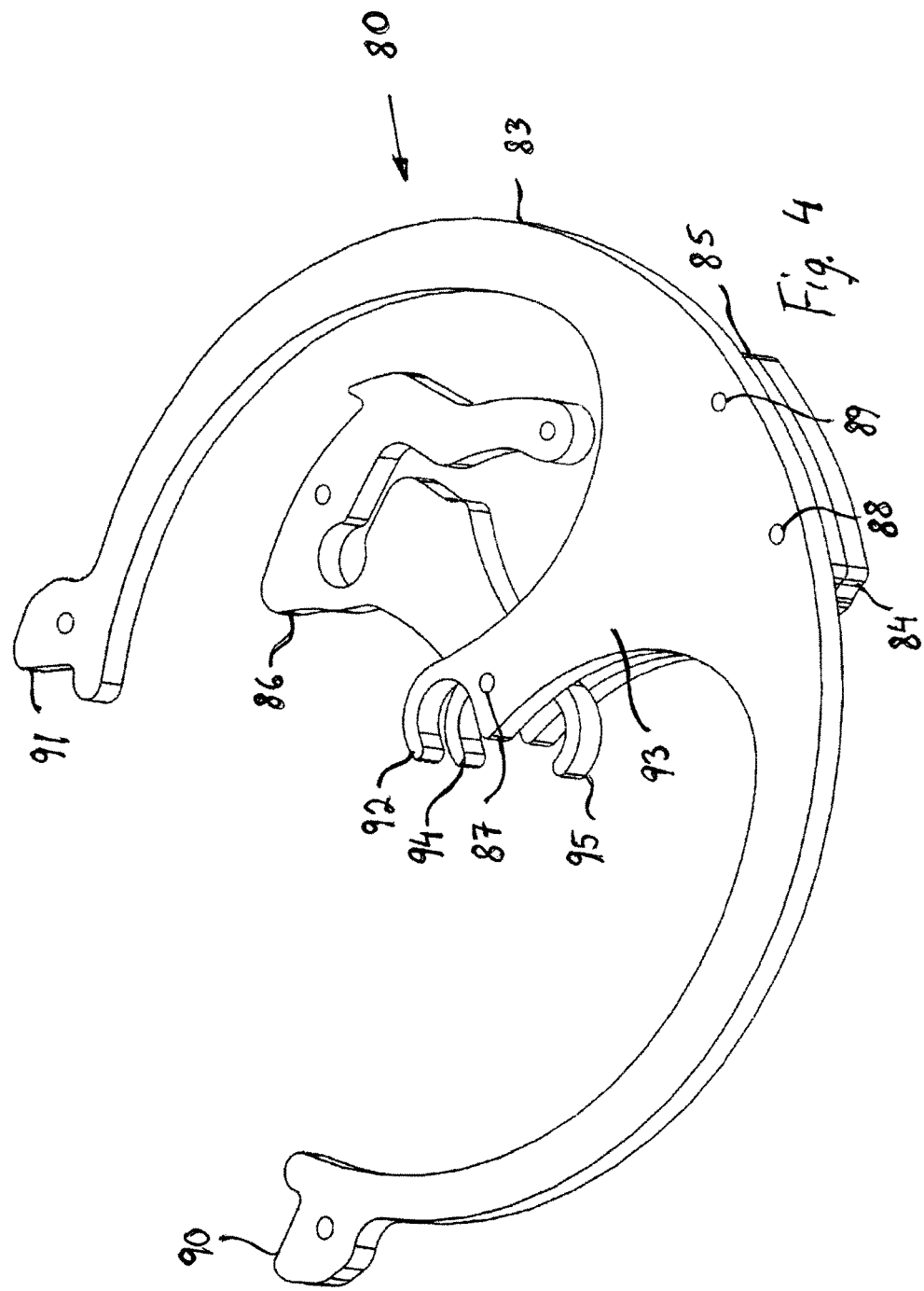
FIG. 4 is a perspective view of a fixture in the embodiment shown in FIG. 2.

FIG. 4 is a perspective view of a fixture 80 and FIG. 5 is an exploded plan view of the fixture 80. As clearly appears from FIG. 5, the fixture comprises four separate parts 83, 84, 85, 86, which are joined to each other by three screws or rivets or similar means arranged in three holes 87, 88, 89.

The first upper part 83 of the fixture is annular over an arch of three quarter of a circle and has a dimension so that it may be arranged inside the insert 30 as shown in FIG. 2 and resting on the shoulders 40 of each recess 37. The upper part 83 comprises two ears 90 and 91 arranged at a mutual distance of 270° along the periphery of the upper part 83. The ears 90 and 91 are dimensioned and arranged for fitting in two of the rectangular openings 41 while the rest of the fixture 80 rests on the shoulders 40.

In the centrum of the fixture, there is arranged a support jaw 92 at the end of an arm 93 extending from the central portion of the first part 83. The support jaw 92 is dimensioned to enclose and retain a tube 81 as will be explained in more detail below. The jaw 92 extends over slightly more than 180° to grip the tube 81 with a friction grip. By this arrangement, the tube gripped by the support jaw 92 will be positioned in the middle of the enclosure 20. A second part 84 is arranged below the arm 93 with a distance and has the same shape as the arm 93 and comprises a support jaw 94. A third part 85 and a fourth part 86 are arranged between the arm 93 and the second part 84. The fourth part 86 has a locking jaw 94 similar to the support jaws 92 and 94 but facing in the opposite direction.

Figure 6:
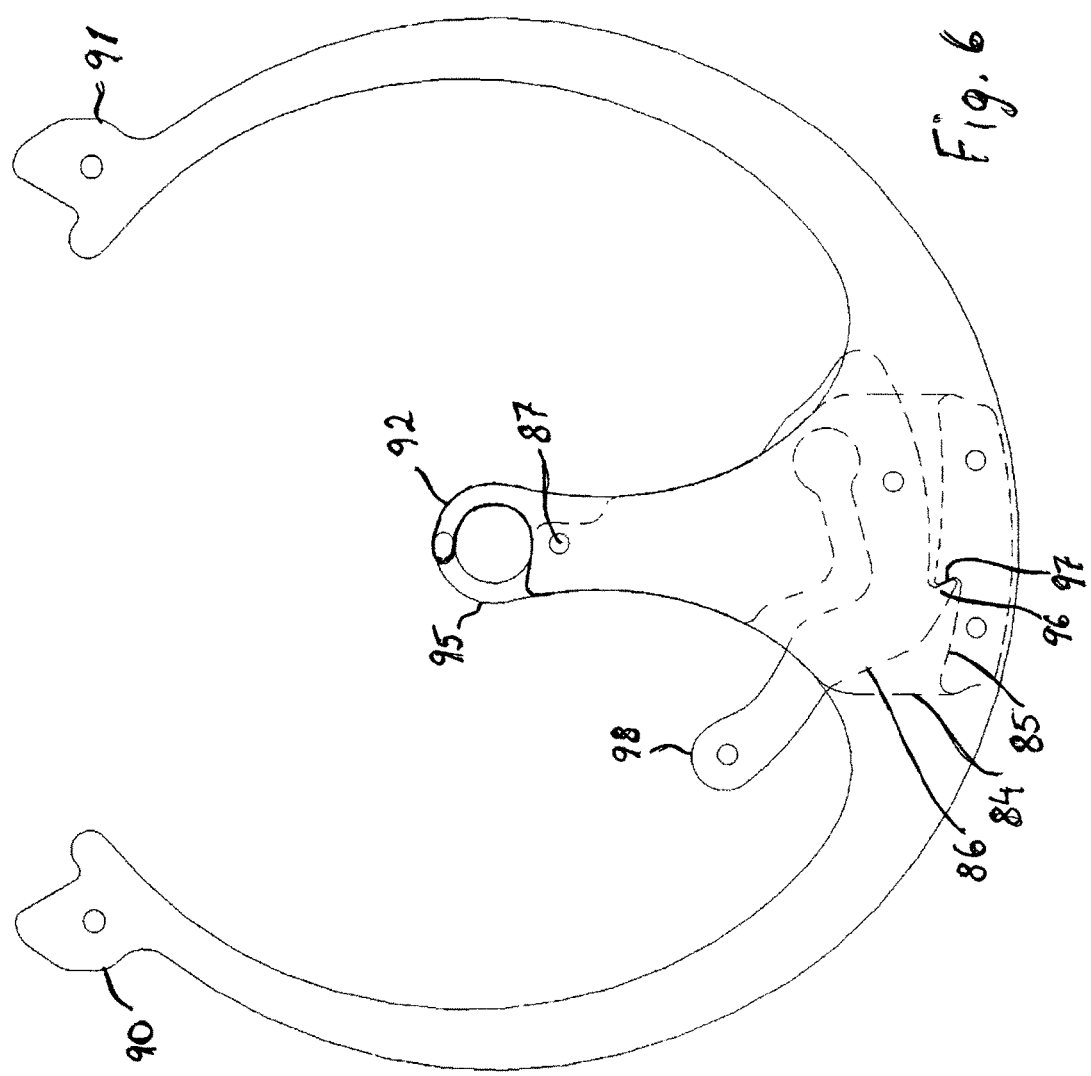
FIG. 6 is a plan view of the fixture according to FIG. 4 in a locked position.

The fourth part 86 is pivotible between an open position as shown in FIG. 4 to a closed position shown in FIG. 6. In the closed position, the fourth part 86 is locked by the third part 85 by a hook system 96, 97. The hook system may be released by a lever 98.

Figure 7:
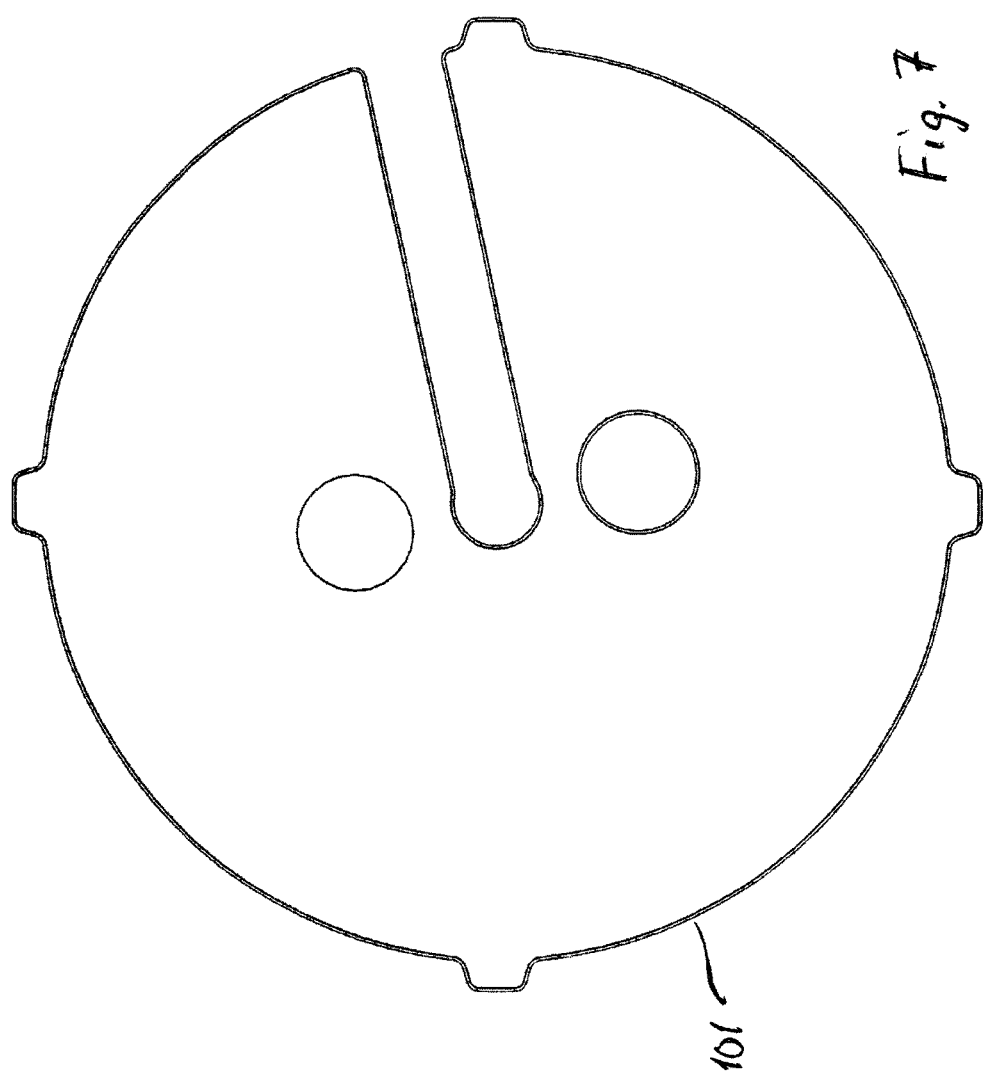
FIG. 7 is a plan view of a lid in the embodiment shown in FIG. 2.

Finally, FIG. 7 shows a lid 101 to be arranged above support fixture 80.

FIGS. 8 to 13 explain the use of the described insert.

Figure 8:
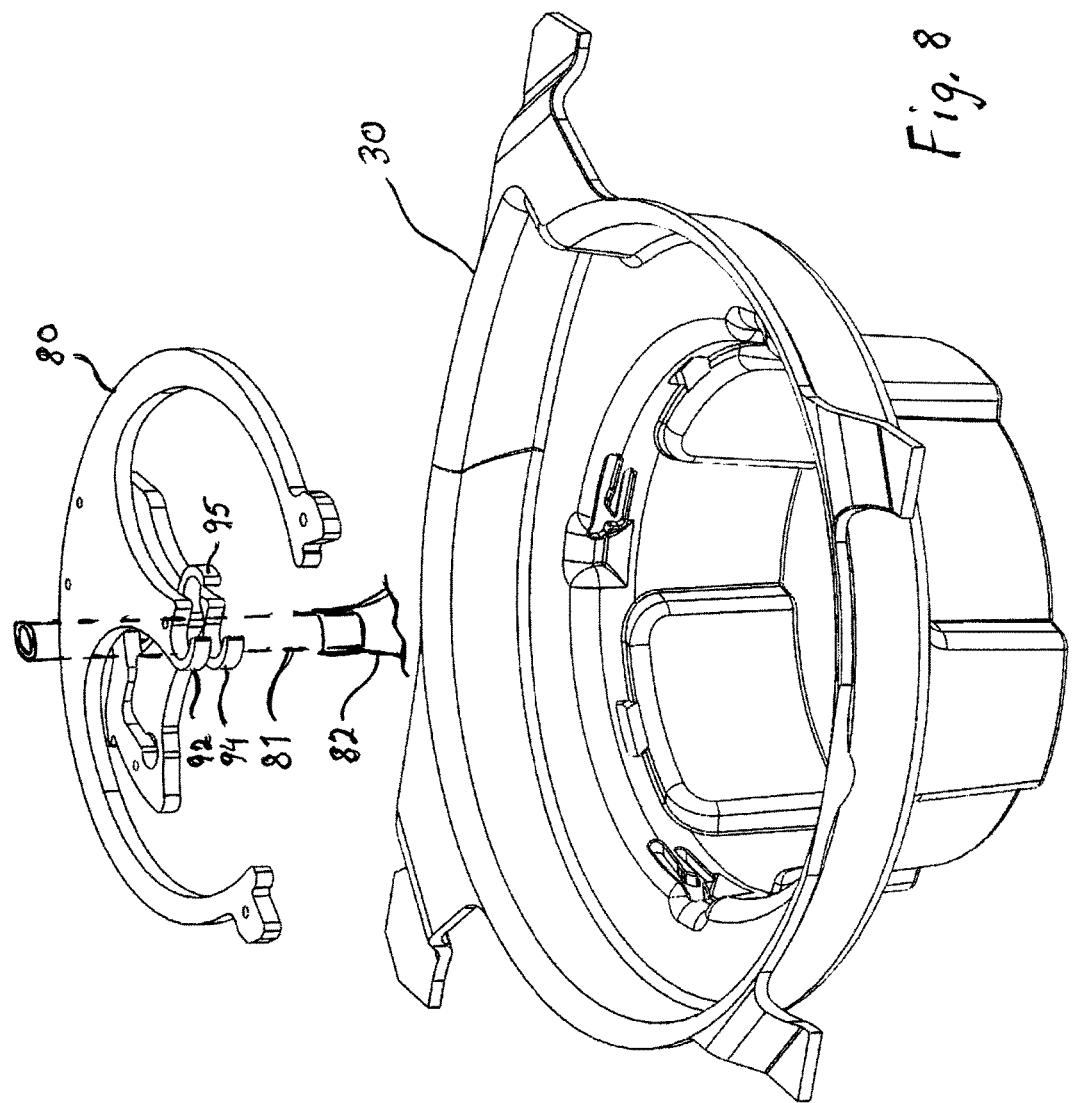
FIG. 8 is a perspective view of the insert and fixture of the embodiment of FIG. 2 and shows the insert and fixture in an initial position for gripping a tube with an organ hanging in the tube.

In FIG. 8, the insert 30 is arranged in an enclosure (not shown) in the manner shown in FIG. 2. The residue of the aorta 82 of the heart has been connected to a tube 81.

The tube 81 is inserted in the support jaws 92 and 94 of the fixture 80 as shown in FIG. 8. The height position of the heart is adjusted as desired by moving the tube 81 in the height direction as seen in FIG. 8. Normally, it is desired that the heart hangs in the tube 81 slightly above the bottom of the enclosure 20, but the user has full control of the height position and may choose another height position.

Figure 9:
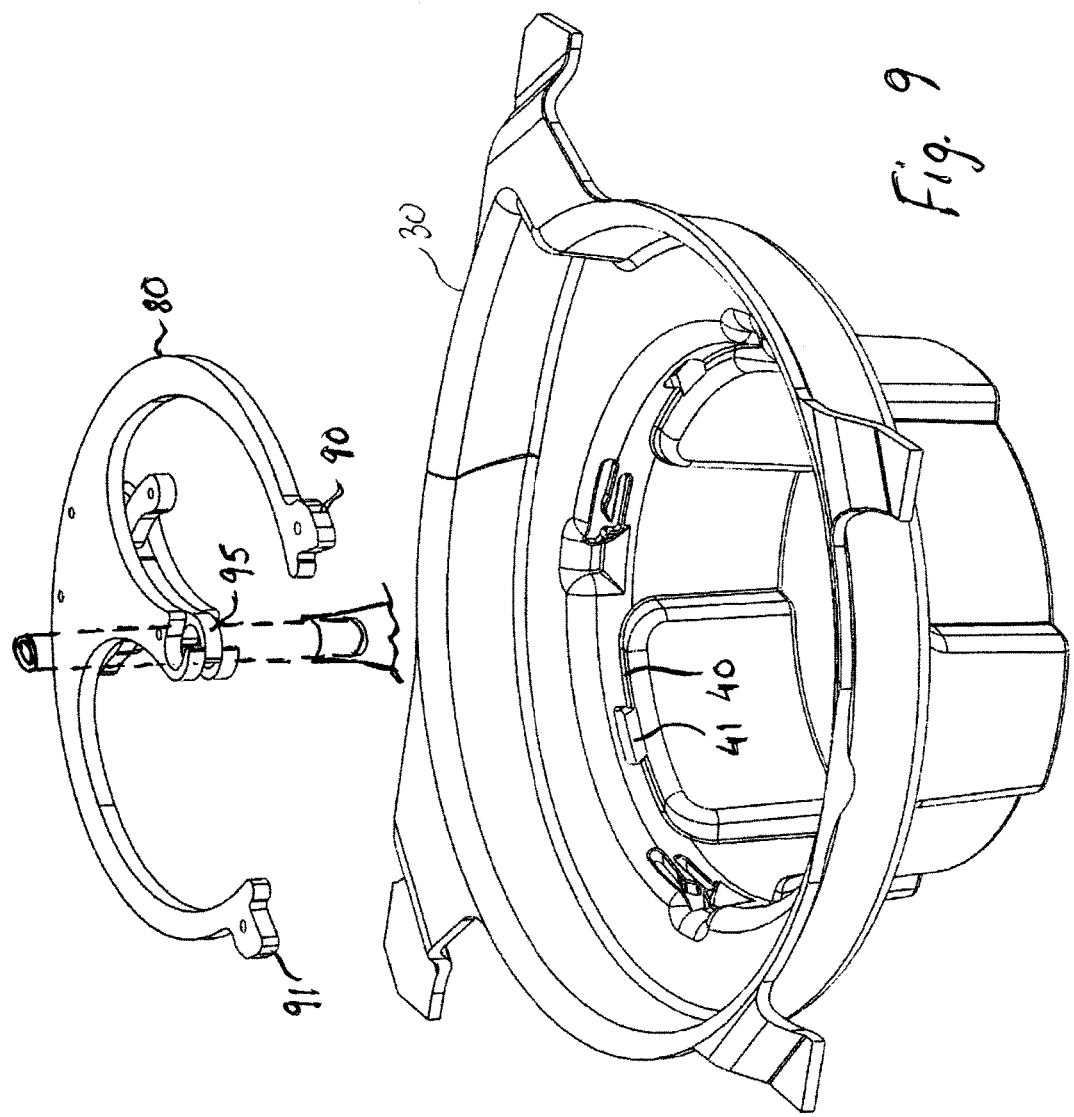
FIG. 9 is a perspective view similar to FIG. 8 with the fixture in a second position.

When the desired position has been obtained, the locking jaw 95 is pivoted to a locked position shown in FIG. 9. The hook system 96 and 97 locks the fourth part 86 in the locked position.

Figure 10:
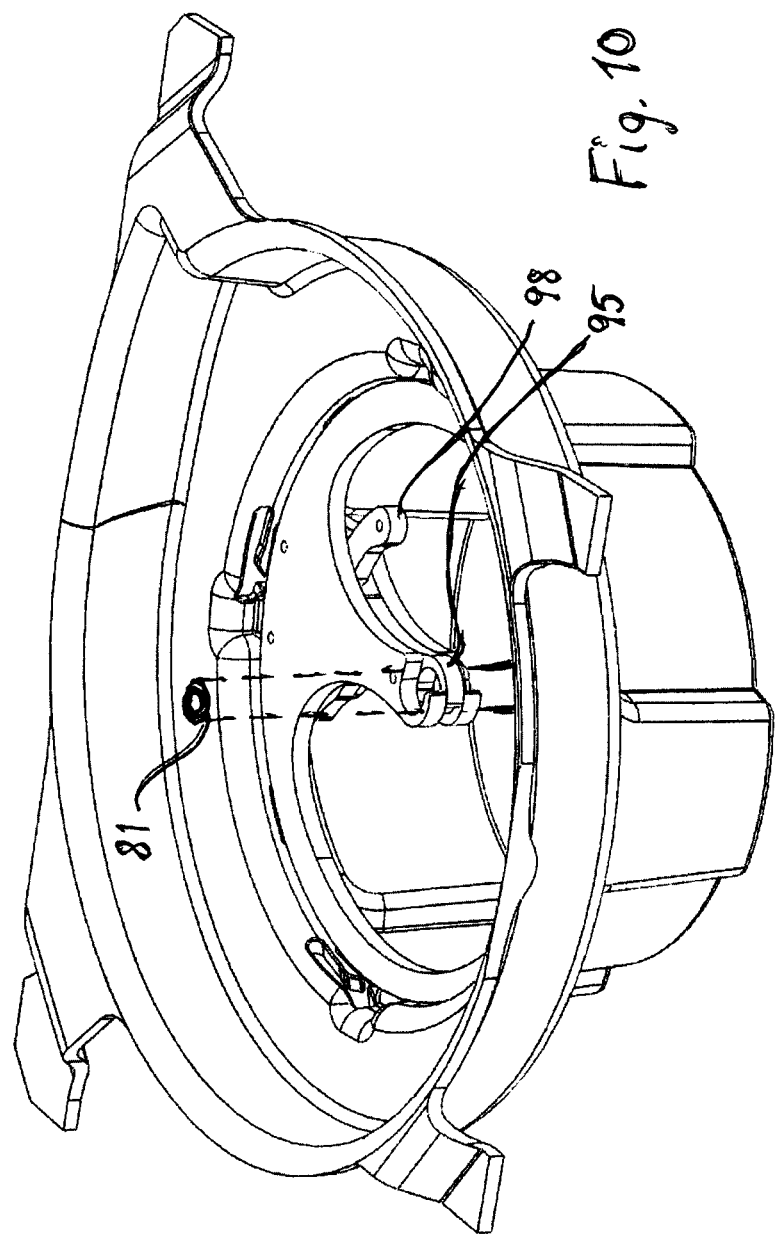
FIG. 10 is perspective view similar to FIG. 8 with the fixture in a third position.

FIG. 10 shows the fixture 80 after being lowered and arranged in the insert 30. The ears 90 and 91 of the fixture 80 are arranged in the rectangular openings 41 while the rest of the fixture rests on the shoulders 40. If it is desired to adjust the position of the heart, this can be done by activating the lever 98, thereby releasing the locking jaw 95, whereupon the height position of the tube 81 and the heart can be adjusted up or down. Then, the lever 98 is moved to the locked position.

Figure 11:
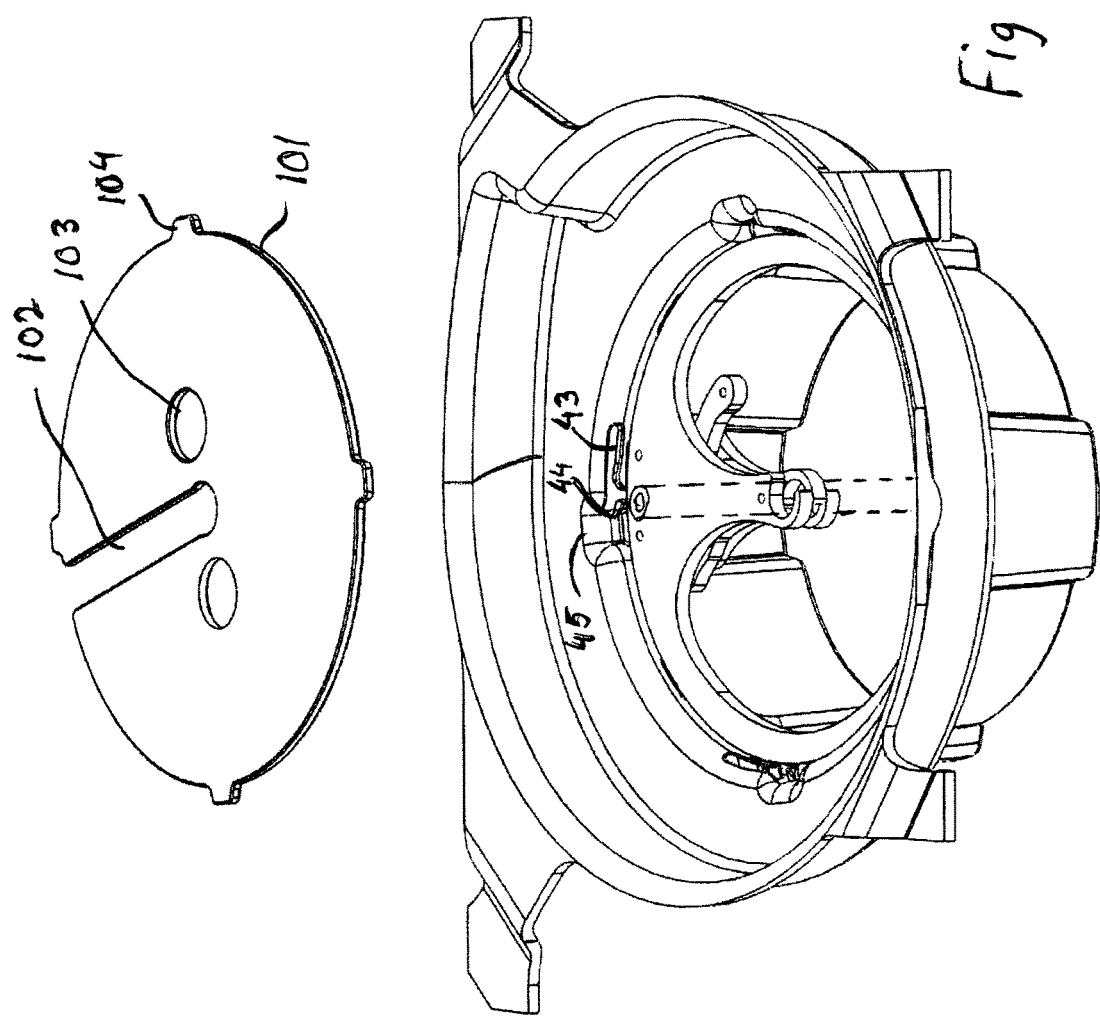
FIG. 11 is perspective view similar to FIG. 8 with the fixture in place and a lid being arranged for closing the space.
Figure 12:
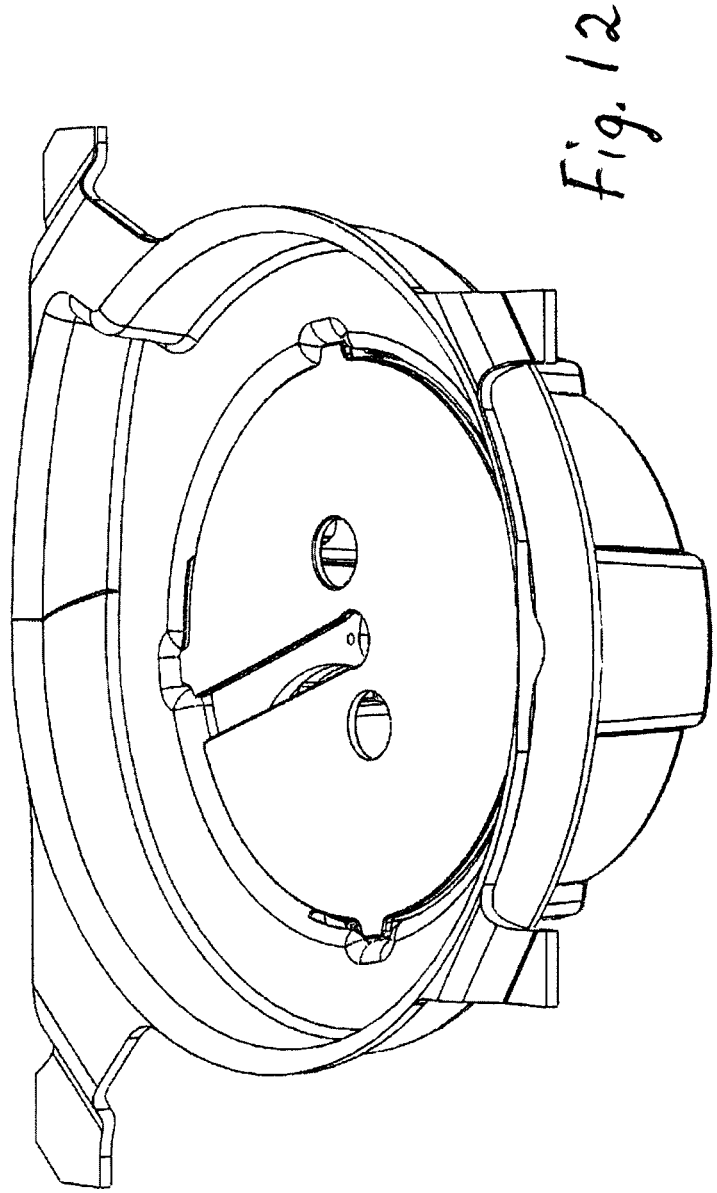
FIG. 12 is a perspective view similar to FIG. 11 with the lid in a second position.

It may be desired to arrange a lid 101 above the insert 30 as shown in FIG. 11. The lid comprises a slit 102, arranged to pass the tube 81 from the periphery to the center of the lid 101. Two grip holes 103 are arranged for handling the lid by two fingers of the user. In addition, there are four tabs 104 arranged equidistantly along the periphery of the lid. The lid and the tabs 104 are arranged and dimensioned to fit in the four slits 43 arranged in the insert 30. The lid 101 is moved so that the tube 81 is arranged in the slit 102 and the tabs 104 are moved down the recesses 45 as shown in FIG. 12.

Figure 13:
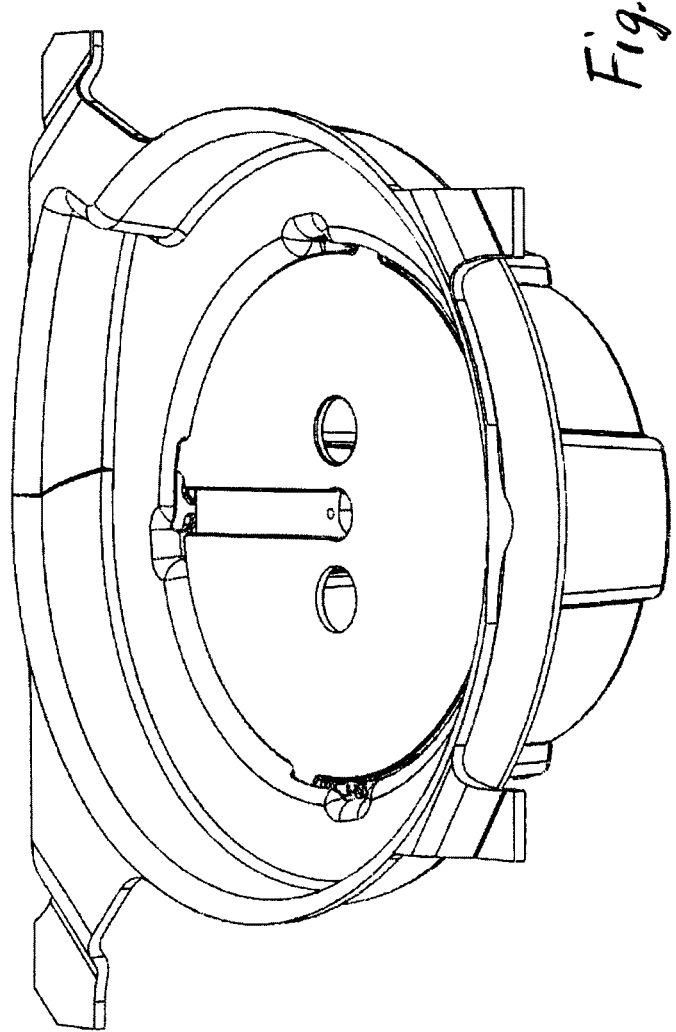
FIG. 13 is a perspective view similar to FIG. 11 with the lid in a final locked position.
Figure 14:
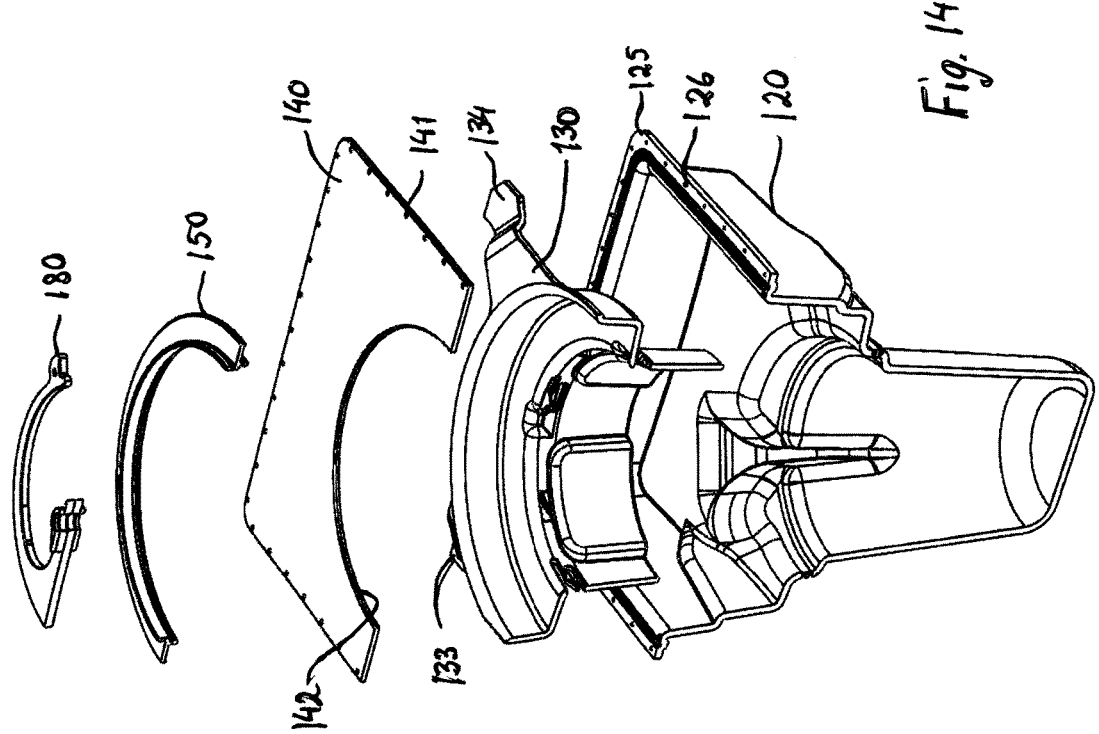
FIG. 14 is an exploded perspective view of an alternative embodiment of the device according to the invention.

Finally, the lid 101 is pivoted clockwise as shown in FIG. 13 for moving the tabs 104 via the side entrances 44 into the slits 43, wherein the lid 101 is locked in place and locks the fixture so that it cannot be removed. In the final position, the slit 102 of the lid is arranged above the arm 93, so that no fluid may pass out through the slit 102.

The fixture 80 and the lid 101 may be arranged in four different positions displaced 90° in relation to each other.

The fixture and lid are constructed so that they can be operated by one hand of the user, so that the user can use the other hand for manipulating the organ to a desired position.

The tube 81 may be provided with a coupling (not shown) for connection to a tube system as shown in FIG. 1. The tube 81 may be connected to the tube system just below the bifurcation of the tubes shown in FIG. 1. Other arrangements may be foreseen, but such arrangements are not the subject of the present invention.

The same system for circulating a fluid as disclosed in WO 2012/128696 A1 may be used in the device according the present invention. However, another circulation system may be used, and such systems are not the subject of the present invention.

If two tubes are used as disclosed in WO 2012/128696 A1, such tubes may enter the insert 30 via two holes 46, 47 in the upper cylindrical portion 39 as shown in FIG. 3.

The insert 30, the fixture 80 and the lid 101 may be disposable parts used once and then discarded. The parts should be sterilized before use.

A second embodiment of the device according to the invention is shown in FIGS. 14 to 19. The second embodiment comprises an enclosure 120 similar to the enclosure 20 and an insert 130 similar to insert 30.

The enclosure 120 is provided with an upper rim 125, which is provided with a plurality of holes 126. A rectangular plate 140 having the same plurality of holes 141 is attached to the enclosure 120 and is tightened to the enclosure by a plurality of screws, not shown. The rectangular plate is provided with a circular opening 142 having a slightly smaller dimension than the insert 130. Thus, the plate 140 locks the insert in place.

A circular rim or collar 150 may be inserted in the opening 142 for attaching a sterile cloth to the upper surface of the device.

Figure 15:
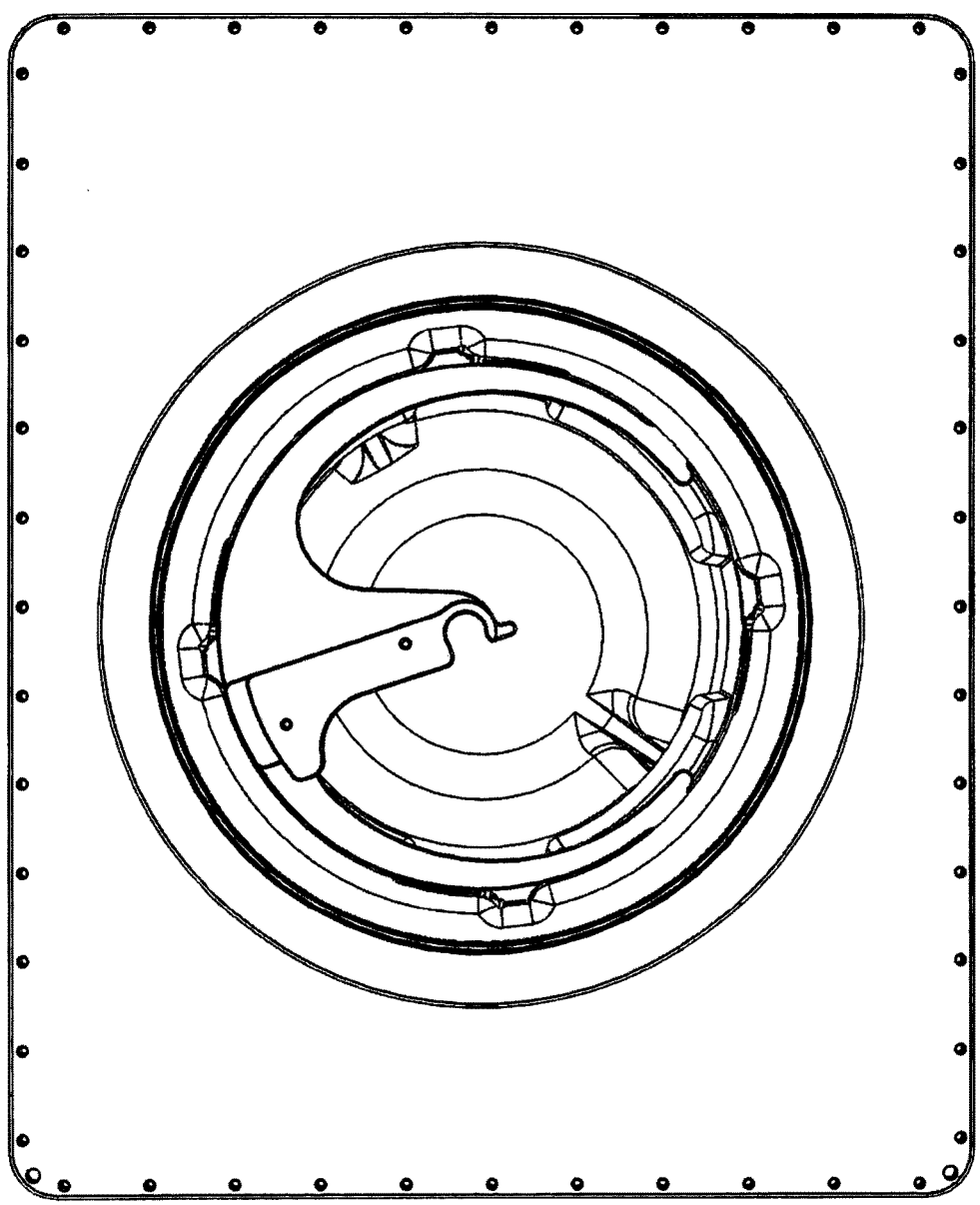
FIG. 15 is a plan view of the embodiment shown in FIG. 14.
Figure 16:
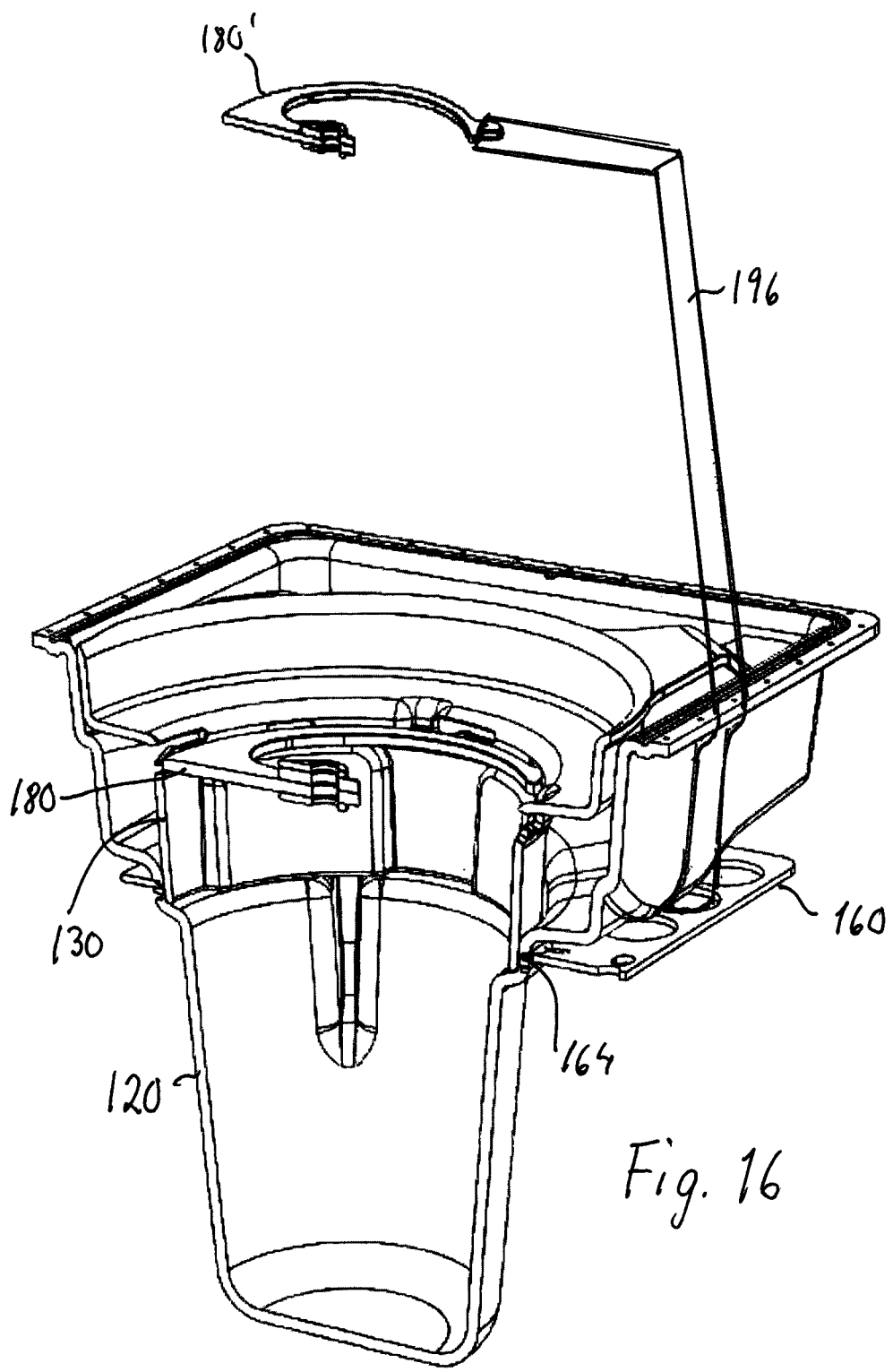
FIG. 16 is a partially cut perspective view of the embodiment shown in FIG. 14 in an assembled state.

FIG. 15 shows the second embodiment in an assembled condition, from above, while FIG. 16 is a broken perspective view, showing the enclosure 120, the insert 130 and the fixture 180.

Figure 17:
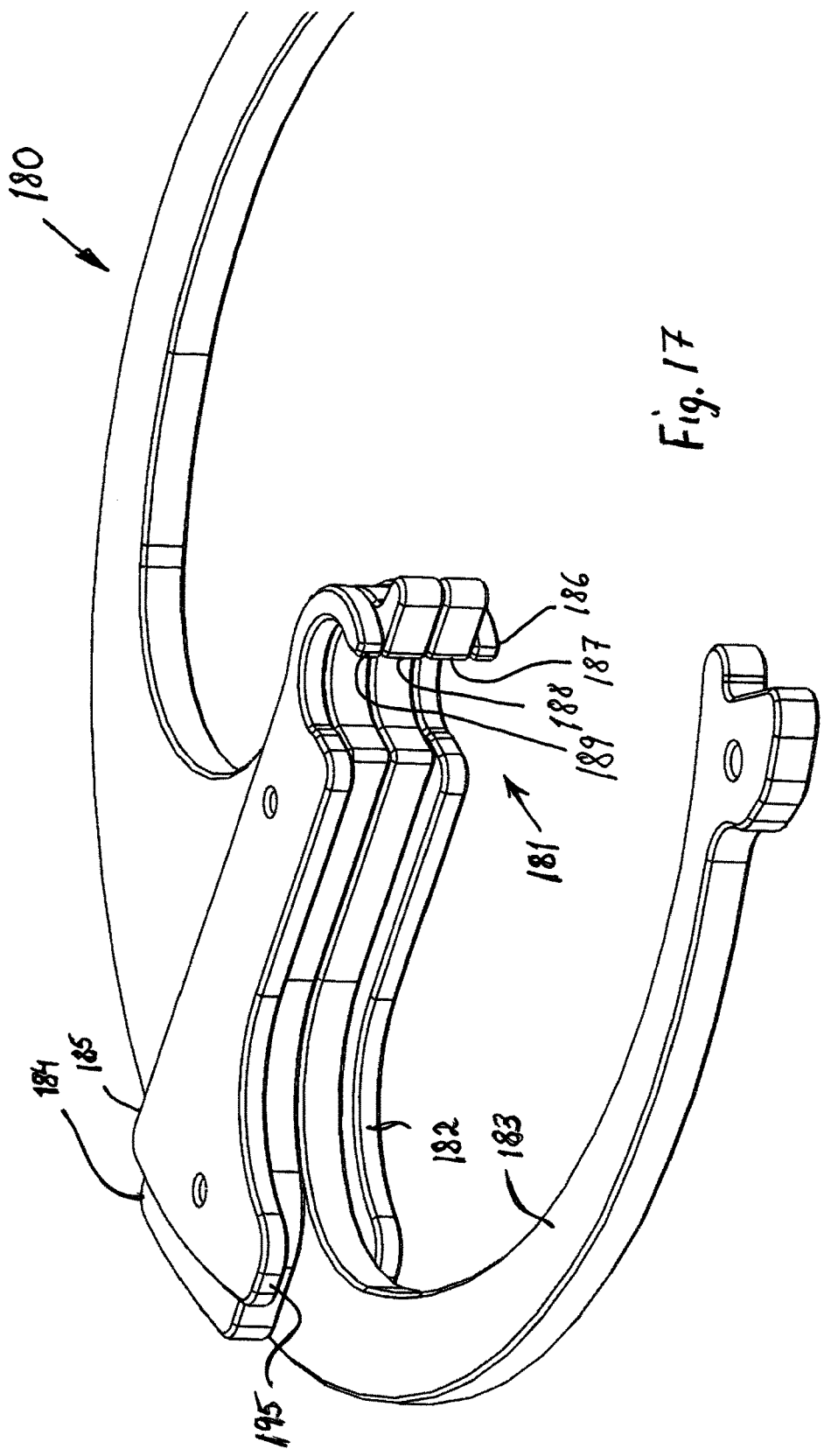
FIG. 17 is a perspective view of the fixture in the embodiment shown in FIG. 14.

FIG. 17 shows the fixture 180 according to the second embodiment. In contrast to the fixture 80, it does not have any moveable part, but the tube is kept in a central recess 181 by a friction grip. The fixture comprises four layers 182, 183, 184, 185, each being provided with a recess 186, 187, 188, 189. The recesses 187, 188 in the middle extend over 180° or slightly more, such as 185°, while the upper and lower recesses 189, 186 extend over a larger bow, such as 190° to 195°. Thus, a tube inserted in the recess is kept by friction by all four recesses and is stopped from passing out of the recesses mainly by the lower 186 and upper 189 recesses.

Figure 18:
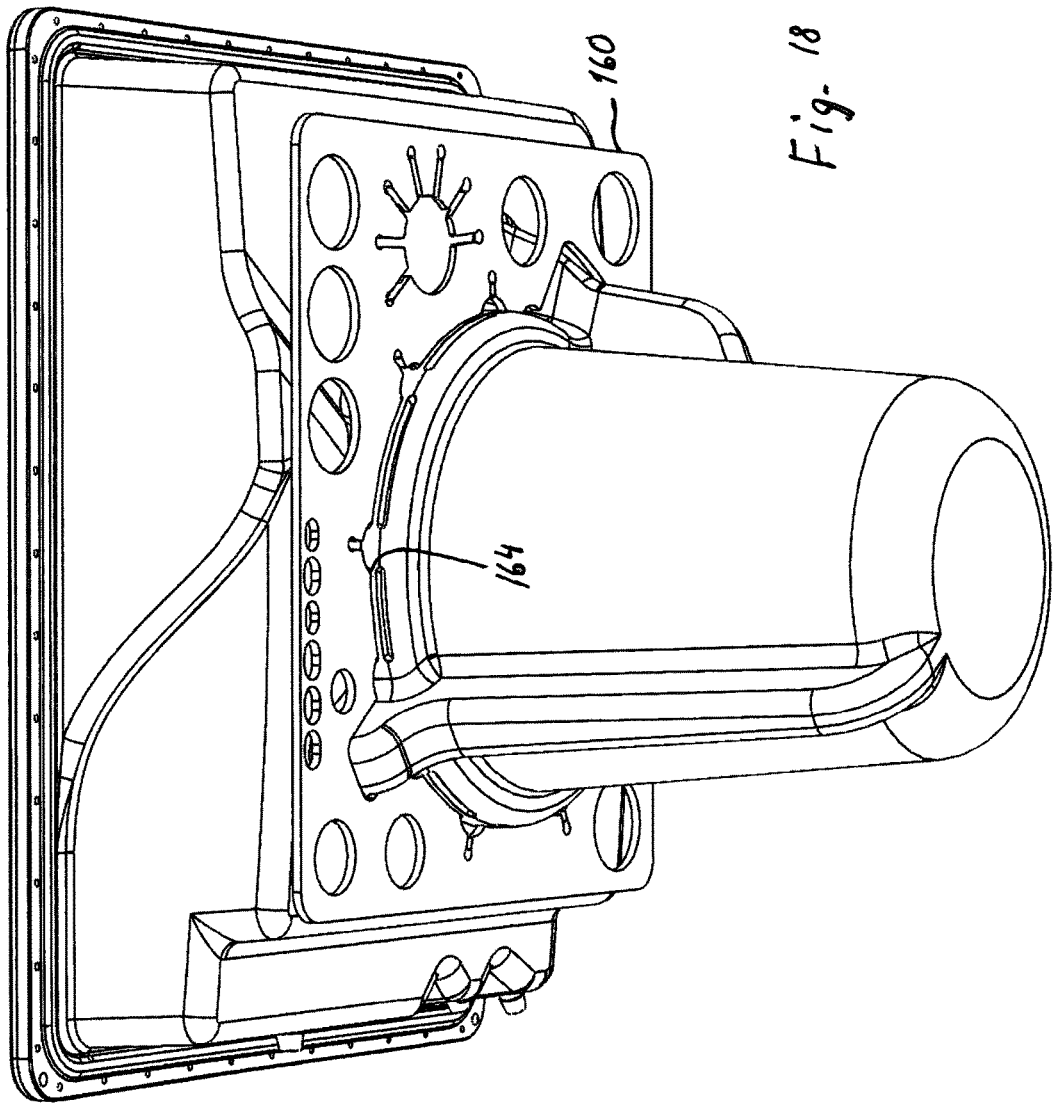
FIG. 18 is a perspective view from below of the embodiment shown in FIG. 14 and showing a support plate.
Figure 19:
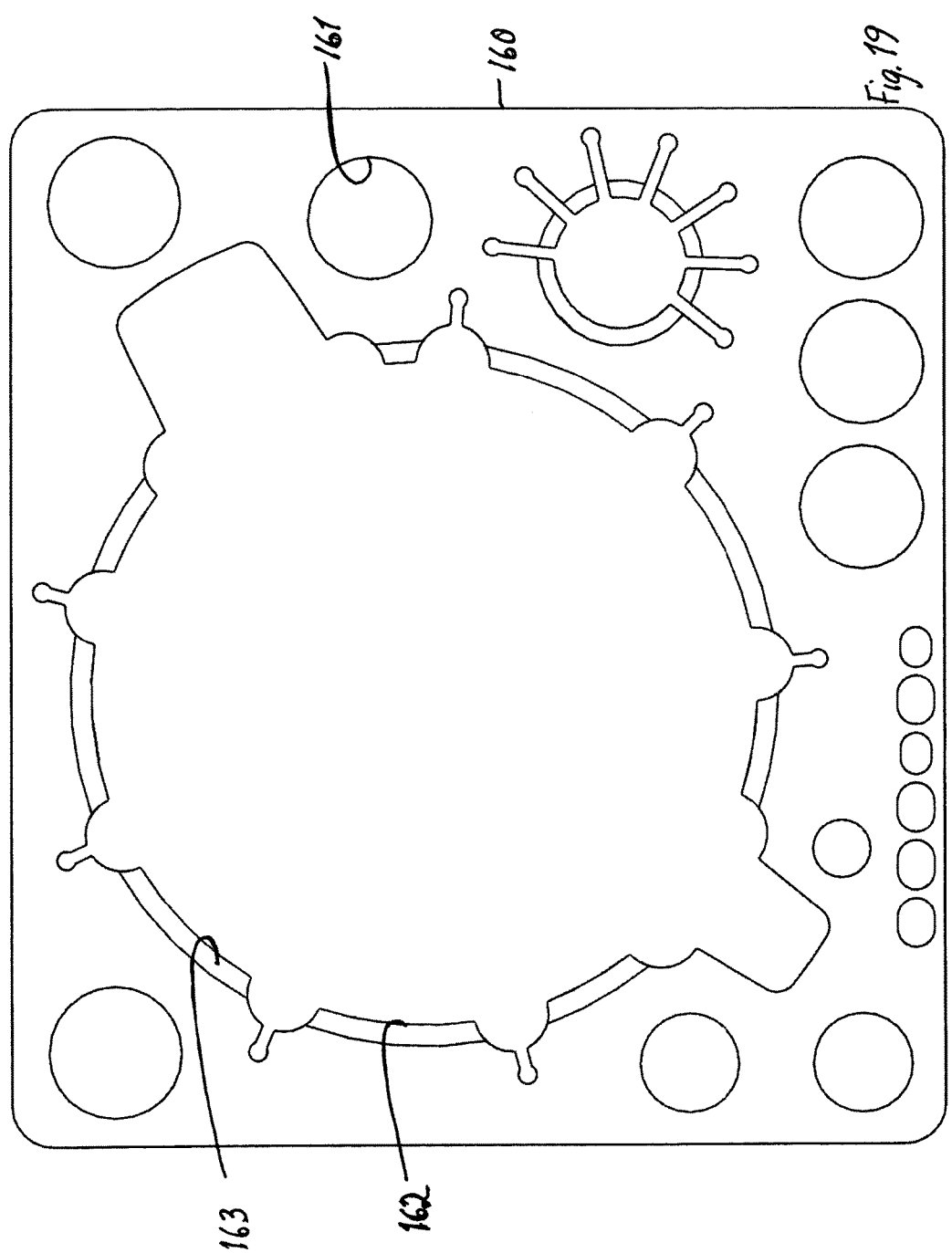
FIG. 19 is a plan view of the support plate according to FIG. 18.

Turning again to FIG. 16, there is shown a support plate 160, which support plate is also shown in FIGS. 18 and 19. The support plate 160 comprises several holes and openings 161 for supporting devices, such as oxygenators, filters and tube sets etc. A circular opening 162 is arranged for fitting outside the bottom portion of the enclosure 120. The inner periphery of the opening 162 is provided with several chamfered peripheral portions 163, which fit into recesses 164 in the outer surface of the enclosure 120, see FIG. 16 and FIG. 18.

As further shown in FIG. 16, the support plate 160 may support a stand 196 for supporting the fixture 180' in a raised position. The distance between the raised fixture 180' and the top surface of the enclosure is substantially the same as the depth of the enclosure 120. The heart may be attached to the fixture 180' in the raised position and the height position be adjusted to a desired position, whereupon the fixture 180' is moved down to the final position shown by the fixture 180 in FIG. 16. In this manner, the distance between the heart and the bottom surface of the enclosure 120 can be adjusted in advance. The stand 196 may be attached to the support plate 160 as shown, or alternatively to the collar 150 shown in FIG. 14. The stand 196 may be removed after use.

The raised position may be in relation to the top surface of the enclosure 120 as defined by the plate 140. Alternatively, the lid 190 shown in FIG. 20 may be put in place for defining the raised distance corresponding to the bottom of the enclosure. After the heart has been arranged in a desired position with the fixture in the raised position and with the lid in place, the lid is removed and the fixture is moved to the final position and the lid is again put in place now above the fixture and the heart.

Figure 20:
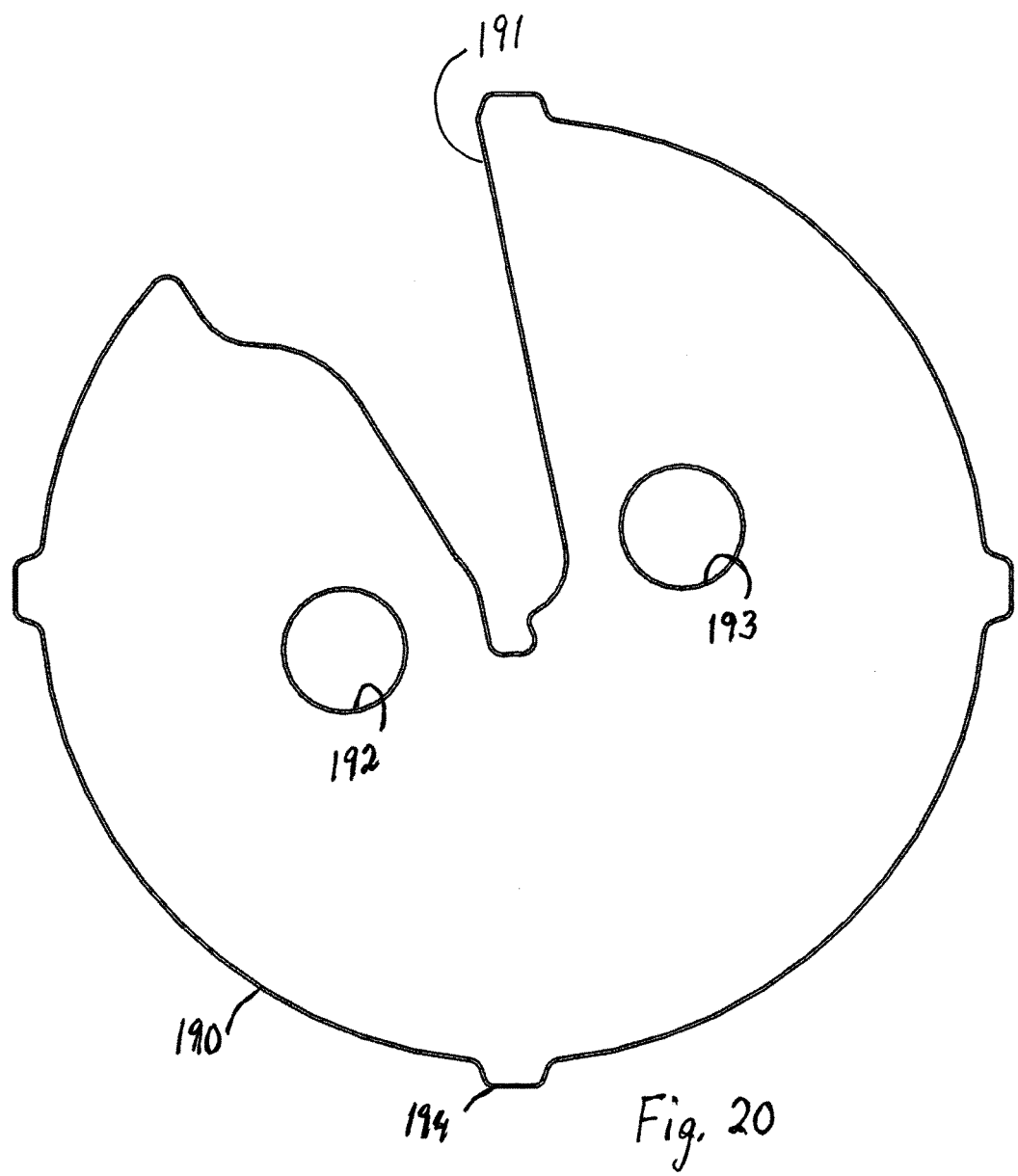

FIG. 20 shows a lid 190 similar to lid 101 shown in FIG. 11. However, lid 190 has a wider slit 191. In addition, the lid has two grip holes 192, 193 and four tabs 194. FIG. 21 shows the lid arranged upon the fixture 180 in an initial position. FIG. 22 shows the lid rotated so that a portion of the lid is positioned below a shoulder 195 of layer 185 of the fixture. In this position, the lid locks the tube in place as desired.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. A device for arranging a harvested organ to be stored in an enclosure before transplantation, whereby the organ is connected to a tube for supply of a medical fluid to the organ, the device comprising:
   a substantially cylindrical insert having a bottom rim being arranged to rest on a shoulder or being arranged just above the shoulder of the enclosure for the organ; and
   a fixture connected to and maintained in a predetermined position inside the insert, for immobilizing the tube in a central position of the insert; wherein the fixture includes,
     an arm extending from the periphery of the fixture to the center of the fixture, a jaw device arranged at the end of the arm and being dimensioned for enclosing and retaining and gripping the tube and maintaining the tube and an organ attached to the tube in an adjustable predetermined height position relative to the fixture, and two ears arranged at the fixture for co-operation with openings arranged in the insert for maintaining the fixture in said predetermined position in relation to the insert.

2. The device according to claim 1, further comprising:
a locking jaw for co-operation with the jaw device for locking the tube against unintentional withdrawal from the jaw device.

3. The device according to claim 1, further comprising:
a lid arranged above the fixture for locking the fixture in position and for closing the space below the fixture.

4. The device according to claim 1, further comprising:
a stand for maintaining the fixture in a raised position for immobilizing the tube and an organ attached to the tube at a predetermined distance above said enclosure, the fixture being constructed to support the organ when said fixture is attached to said stand at a position corresponding to said predetermined position inside the insert when said fixture is inserted into the insert.

5. The device according to claim 1, wherein the organ is a heart and the tube is attached to an aorta residue of the heart.

6. A device for arranging a harvested organ to be stored in an enclosure before transplantation, whereby the organ is connected to a tube for supply of a medical fluid to the organ, the device comprising:

a substantially cylindrical insert having a bottom rim being arranged to rest on a shoulder or being arranged just above the shoulder of the enclosure for the organ; and a fixture which is connected to and maintained in a predetermined position inside the insert, for immobilizing the tube in a central position of the insert; and wherein the fixture includes, an arm extending from the periphery of the fixture to the center of the fixture, a jaw device arranged at the end of the arm and being dimensioned for enclosing and retaining and gripping the tube and maintaining the tube and an organ attached to the tube in an adjustable predetermined height position relative to the fixture, and a first upper part which is annular over an arch of three quarter of a circle and has a dimension constructed to be arranged inside the insert, and the upper part includes two ears arranged at a mutual distance of 270° along the periphery of the upper part; the ears being dimensioned and arranged for fitting in rectangular openings of the insert while the rest of the fixture rests on shoulders of the insert.

7. The device according to claim 6, further comprising:
a stand for maintaining the fixture in a raised position for immobilizing the tube and an organ attached to the tube at a predetermined distance above said enclosure, whereupon the fixture is constructed to be connected to said insert in said predetermined position inside the insert.

* * * * *